(12) United States Patent
Lawrenson

(10) Patent No.: US 10,471,226 B2
(45) Date of Patent: Nov. 12, 2019

(54) PATIENT INTERFACE WITH AUTOMATIC POSITION ADJUSTMENT

(71) Applicant: KONINKLIJKE PHILIPS N.V., Eindhoven (IL)

(72) Inventor: Matthew John Lawrenson, Bussigny-pres-de-lausanne (CH)

(73) Assignee: Koninklijke Philips N.V., Eindhoven (NL)

( * ) Notice: Subject to any disclaimer, the term of this patent is extended or adjusted under 35 U.S.C. 154(b) by 555 days.

(21) Appl. No.: 15/120,870

(22) PCT Filed: Feb. 9, 2015

(86) PCT No.: PCT/EP2015/052570
§ 371 (c)(1),
(2) Date: Aug. 23, 2016

(87) PCT Pub. No.: WO2015/128173
PCT Pub. Date: Sep. 3, 2015

(65) Prior Publication Data
US 2016/0361512 A1    Dec. 15, 2016

(30) Foreign Application Priority Data
Feb. 26, 2014   (EP) .................................... 14156826

(51) Int. Cl.
*A61M 16/06*    (2006.01)
(52) U.S. Cl.
CPC .... *A61M 16/0605* (2014.02); *A61M 16/0683* (2013.01); *A61M 16/0633* (2014.02);
(Continued)

(58) Field of Classification Search
CPC . A61B 5/04085; A61B 5/0476; A61B 5/0492; A61B 5/0878; A61B 5/6803;
(Continued)

(56) References Cited

U.S. PATENT DOCUMENTS 7,025,730 B2 * 4/2006 Cho ..................... A61N 1/3601
600/529
9,687,624 B2 * 6/2017 Haas ..................... A61M 16/06
(Continued)

FOREIGN PATENT DOCUMENTS

CN           203208491 U      9/2013
WO      WO2013133850 A1      9/2013
(Continued)

*Primary Examiner* — Annette Dixon
(74) *Attorney, Agent, or Firm* — Michael W. Haas

(57) ABSTRACT

The present invention relates to a patient interface (10) for delivering a flow of breathable gas to a patient (12), comprising: a sealing portion (22) for sealing an interface between the patient interface (10) and a patient's face when the patient (10) interface is worn by the patient (12); a detection unit (30) including a displacement sensor (32, 32') for generating a displacement signal including information on a displacement of the sealing portion (22) with respect to the patient's face relative to an identified reference position of the sealing portion (22) with respect to the patient's face; one or more actuators (36, 36', 36") for positioning at least parts of the sealing portion (22) relative to the patient's face; and a control unit (34) that is configured to actuate the one or more actuators (36, 36', 36") based on the displacement signal in order to adjust a position of at least parts of the sealing portion (22) with respect to the patient's face during use.

15 Claims, 6 Drawing Sheets

(52) U.S. Cl.
CPC ............... *A61M 2205/0283* (2013.01); *A61M 2205/0288* (2013.01); *A61M 2205/10* (2013.01); *A61M 2205/13* (2013.01); *A61M 2205/15* (2013.01); *A61M 2205/332* (2013.01); *A61M 2205/3306* (2013.01); *A61M 2205/3313* (2013.01); *A61M 2205/3317* (2013.01); *A61M 2205/3331* (2013.01); *A61M 2205/502* (2013.01); *A61M 2205/52* (2013.01); *A61M 2205/702* (2013.01); *A61M 2230/00* (2013.01); *A61M 2230/63* (2013.01)

(58) Field of Classification Search
CPC ............ A61M 16/0051; A61M 16/021; A61M 16/024; A61M 16/06; A61M 16/0605; A61M 16/0611; A61M 16/0622; A61M 16/0633; A61M 16/0655; A61M 16/0683; A61M 16/0694; A61M 16/0858; A61M 2016/0027; A61M 2016/0661; A61M 2205/0238; A61M 2205/10; A61M 2205/13; A61M 2205/15; A61M 2205/3306; A61M 2205/3317; A61M 2205/332; A61M 2205/3344; A61M 2205/3368; A61M 2205/3375; A61M 2205/3584; A61M 2205/3592; A61M 2205/502; A61M 2205/52; A61M 2205/581; A61M 2205/583; A61M 2205/6018; A61M 2205/702; A61M 2230/04; A61M 2230/08; A61M 2230/10; A61M 2230/205; A61M 2230/30; A61M 2230/50; A61M 2230/60; A61M 2230/62; A61M 2230/63; A61N 1/3601; A61N 1/36514

See application file for complete search history.

(56) References Cited

U.S. PATENT DOCUMENTS

| | | | |
|---|---|---|---|
| 2004/0163648 A1* | 8/2004 | Burton | ............... A61B 5/04085 128/204.21 |
| 2007/0163594 A1 | 7/2007 | Ho et al. | |
| 2012/0080035 A1 | 4/2012 | Guney | |
| 2012/0240933 A1* | 9/2012 | Haas | ..................... A61M 16/06 128/204.21 |
| 2012/0291785 A1 | 11/2012 | Ramanan et al. | |
| 2013/0056004 A1 | 3/2013 | Bowditch | |
| 2013/0118500 A1 | 5/2013 | Stevens | |
| 2015/0224275 A1* | 8/2015 | Pastoor | ............. A61M 16/0611 128/205.25 |

FOREIGN PATENT DOCUMENTS

| | | | | |
|---|---|---|---|---|
| WO | WO2013183018 | | 12/2013 | |
| WO | WO-2014024086 A1 * | | 2/2014 | ........ A61M 16/0611 |

* cited by examiner

PATIENT INTERFACE WITH AUTOMATIC POSITION ADJUSTMENT

CROSS-REFERENCE TO RELATED APPLICATIONS

This patent application claims the priority benefit under 35 U.S.C. § 371 of international patent application no. PCT/EP2015/052570, filed Feb. 9, 2015, which claims the benefit of European Patent Application No. EP14156826.1, filed on Feb. 26, 2014. These applications are hereby incorporated by reference herein.

FIELD OF THE INVENTION

The present invention relates to a patient interface for delivering a flow of breathable gas to a patient. The present invention particularly relates to a patient interface with an automatic position adjustment. Furthermore, the present invention relates to a pressure support system including such a patient interface.

BACKGROUND OF THE INVENTION

Patient interfaces, such as masks for covering the mouth and/or nose, are used for delivering gas to a patient. Such gases, like air, cleaned air, oxygen, or any modification of the latter, are submitted to the patient via the patient interface in a pressurized or unpressurized way.

For several chronic disorders and diseases, a long-term attachment of such a patient interface to a patient is necessary or at least advisable.

One non-limiting example for such a disease is obstructive sleep apnea or obstructive sleep apnea syndrome (OSA). OSA is usually caused by an obstruction of the upper airway. It is characterized by repetitive pauses in breathing during sleep and is usually associated with a reduction in blood oxygen saturation. These pauses in breathing, called apneas, typically last 20 to 40 seconds. The obstruction of the upper airway is usually caused by a reduced muscle tonus of the body that occurs during sleep. The human airway is composed of walls of soft tissue which can collapse and thereby obstruct breathing during sleep. Tongue tissue moves towards the back of the throat during sleep and thereby blocks the air passages. OSA is therefore commonly accompanied with snoring.

Different invasive and non-invasive treatments for OSA are known. One of the most powerful non-invasive treatments is the usage of Continuous Positive Airway Pressure (CPAP) or Bi-Positive Airway Pressure (BiPAP) in which a patient interface is connected to a pressure generator via a patient circuit including one or more tubes, wherein the pressure generator blows pressurized gas into the patient interface and into the patient's airway in order to keep it open. Positive air pressure is thus provided to a patient by means of the patient interface that is worn by the patient typically during sleep.

Examples for such patient interfaces are:
nasal masks, which fit over the nose and deliver gas through the nasal passages,
oral masks, which fit over the mouth and deliver gas through the mouth,
full-face masks, which fit over both the nose and the mouth and deliver gas to both, and
nasal pillows, which are regarded as patient interfaces as well within the scope of the present invention and which consist of small nasal inserts that deliver gas directly to the nasal passages.

The patient interface is usually positioned and donned to the patient's head using some kind of headgear. Wearing a patient interface can be uncomfortable, since for providing an airtight seal between the patient interface and the patient's face, the patient interface has to be worn with a sufficient level of pressure on the face. The patient interface also has to be correctly fitted to the patient's face, since a poor fit of the patient interface will lead to a loss of pressure which can negatively affect the therapeutic treatment.

Whilst the patient interface may be correctly fitted prior to sleep, during sleep the user may move into a position where mechanical pressure is exerted onto the patient interface, in particular to the front, protruding section of the patient interface. During sleep the position of the patient interface may, for example, be disturbed by a pillow or other external obstacles. A user turns and the pillow or other external obstacle moves the patient interface, such that leakages may occur at the interface between the patient interface and the patient's face which results in a pressure loss via the ill-fitting sections. However, the provision of pressure in the patient's airway is one of the main purposes of such a patient interface. Hence, such a pressure loss will reduce the effectiveness of the therapeutic treatment. Another cause for a leakage may be the relaxation of the facial muscles as soon as the patient falls asleep. As a consequence, the stiffness of the facial surface changes and induces leakage of the patient interface.

A further problem that may arise when the position of the patient interface is shifted from its original, correctly fitted position is the possible formation of red marks in the patient's face.

Several attempts to solve the above-mentioned problems are known. US 2013/0118500 A1 discloses a method and system for managing a set of active headgear straps for a Positive Airway Pressure (PAP) mask including detecting a gas pressure value within the mask by means of a pressure sensor, analyzing the gas pressure value occurring in the mask with a processor for identifying an adjustment of the set of active headgear straps, and performing the identified adjustment with the set of active headgear straps. In other words, the headgear straps are adjusted in dependence to the gas pressure that occurs within the mask.

WO 2013/183018 A1 discloses a patient interface with a cushion element and an electro-active polymer material that allows to readjust the position of the cushion element upon activation of the electro-active polymer material. The electro-active polymer material is either controlled by means of a temperature sensor that measures the temperature at the interface between the patient interface and the patient's face or it is controlled by means of one or more pressure sensors which measure the pressure at different positions of the interface between the patient interface and the patient's face. The electro-active polymer material is activated if the temperature or the pressure increases above or falls below a certain threshold.

US 2004/0163648 A1 dicloses a gas mask for use with associated monitoring and controlling apparatus. Different types of sensors on or in the mask and straps or caps are therein used for monitoring of patients with sleep disorders, breathing disorders or for anesthesia. These sensors include oximetery sensors, patient position sensors, eye movement sensors, leak detection sensors, EEG, EMG, EOG, ECG, PTT, microphones, pulse, blood pressure, oxygen saturation, temperature, movement sensors, position sensors, light sensors, leak detection sensors and gas delivery sensors.

With regard to the above-mentioned problems there is, however, still room for improvement.

SUMMARY OF THE INVENTION

It is an object of the present invention to provide an alternative and improved patient interface that more effectively overcomes the problem of gas leakages or a red mark formation due to unintentional position shifts of the patient interface during sleep.

According to an aspect of the present invention, a patient interface for delivering a flow of breathable gas to a patient is presented which comprises:
- a sealing portion for sealing an interface between the patient interface and a patient's face when the patient interface is worn by the patient;
- a detection unit including a displacement sensor for generating a displacement signal including information on a displacement of the sealing portion with respect to the patient's face relative to an identified reference position of the sealing portion with respect to the patient's face;
- one or more actuators for positioning at least parts of the sealing portion relative to the patient's face; and
- a control unit that is configured to actuate the one or more actuators based on the displacement signal in order to adjust a position of at least parts of the sealing portion with respect to the patient's face during use.

According to a further aspect of the present invention, a pressure support system is presented which comprises a patient interface of the above-mentioned type and a pressure generator for generating the flow of breathable gas.

Preferred embodiments of the invention are defined in the dependent claims. It shall be understood that the claimed pressure support system has similar and/or identical preferred embodiments as the claimed patient interface and as defined in the dependent claims.

The present invention proposes a way for the patient interface to automatically self-adjust the position in order to regain the optimum position of the patient interface with respect to the patient's face. The patients thus incur less disturbance due to their patient interface being moved whilst sleeping.

A displacement sensor senses an unintentional displacement of the patient interface such that the control unit may actuate one or more actuators for repositioning at least parts of the sealing portion of the patient interface relative to the patient's face in response to a sensed displacement. Depending on how soft/flexible cushion of the mask is there may be an issue that a pillow pushes the harder plastic portion of the mask (e.g. the mask shell) onto the face without the area touching the face moving. The adjustments could protect against this. The displacement sensor particularly senses a displacement of the sealing portion of the patient interface relative to an identified reference position of the sealing portion with respect to the patient's face. The identified reference position is a position in which the sealing portion of the patient interface is correctly fitted onto the patient's face such that no gas leakages occur at the interface between the patient interface and the patient's face. By sensing a displacement from this optimal position and by knowing the optimal position, the control unit is able to readjust the position of the patient interface and bring it back again into its optimal position such that possibly occurring gas leakages will be automatically closed again.

If the patient turns his head during sleep and any external obstacle, such as e.g. a pillow, moves the patient interface away from its optimal position, this will be detected by the displacement sensor and the control unit will actuate the one or more actuators accordingly to bring at least parts of the sealing portion of the patient interface back into its optimal position again. The patient him-/herself might not even recognize this. Since air leakages are automatically closed by means of this technique, the overall therapeutic treatment is significantly improved.

It shall be noted that the electroactive polymer material proposed in WO 2013/183018 A1 may also be used as a sensor. However, in contrast to the displacement sensor used according to the present invention, an electroactive polymer material as described in WO 2013/183018 A1 is only able to sense an absolute pressure applied to the material or an absolute deformation of the material. An electroactive polymer material may not detect a displacement, meaning a covered distance, of the sealing portion with respect to the patient's face, nor does it enable sensing a relative displacement relative to an identified reference position. WO 2013/183018 A1 thus suggest the creation of a massaging effect provided by the electroactive polymer material instead of re-positioning the sealing portion into an identified reference position.

According to an embodiment, the patient interface further comprises a storage unit for storing the identified reference position of the sealing portion with respect to the patient's face.

This allows, for example, storing position coordinates of the reference position of the sealing portion with respect to the patient's face. Instead of position coordinates other distinctive reference features, for example characteristic features in the patient's face that are covered by the sealing portion in the optimal reference position, may be stored in the storage unit. As soon as the displacement sensor senses any deviation from the stored parameters or characteristics of the identified reference position, the control unit may trigger the one or more actuators to readjust at least parts of the sealing portion relative to the patient's face in order to bring the sealing portion back into its optimal position.

According to a further embodiment, the patient interface may further comprise an input interface which is configured to trigger the detection unit to identify and store in the storage unit information on the reference position of the sealing portion with respect to the patient's face upon a manual activation of the input interface by the patient.

The input interface may be realized e.g. as a button that the patient may touch or press as soon as the patient interface is correctly fitted to his/her face. In response to the user touching/pressing said button the displacement sensor may then identify the reference position and store the respective position parameters in the storage unit. As soon as these position parameters change due to an unintentional movement of the sealing portion with respect to the patient's face, the control unit may trigger the one or more actuators to reposition at least parts of the sealing portion relative to the patient's face again in the way explained above.

In an alternative embodiment, the patient interface may further comprise an identification unit for automatically identifying the reference position of the sealing portion with respect to the patient's face when the patient interface is worn by the patient.

The identification unit may e.g. automatically identify the reference position by means of an optical sensor that performs a landmark detection in the patient's face. If the position of the sealing portion of the patient interface corresponds with certain characteristic landmarks in the patient's face, the identification unit may trigger the detection unit to store the position parameters of the current position of the sealing portion as the position parameters of the reference position.

The identification unit may alternatively identify that the sealing portion is in its optimal position (i.e. in the reference position) by means of a pressure sensor that senses the gas pressure within the interior of the patient interface. If said gas pressure is above a certain threshold, this could be an indication that the patient interface is correctly fitted and positioned to the patient's face, so that the position is then identified as reference position.

According to a further alternative, the reference position could be identified as the position which has been reached shortly after the patient interface has been donned to the patient's face, assuming that the patient always correctly positions the patient interface with respect to his/her face. In this case the identification unit could e.g. comprise an accelerometer that measures the movement of the patient interface and triggers the identification unit to identify the reference position as soon as the movements (caused by the manual position adjustments of the patient while donning the patient interface to his/her face) have come to an end.

It shall be noted that in case of an automatic identification of the reference position, a storage unit as explained above is not necessarily needed. The position parameters of the reference position do not necessarily have to be saved. Instead, the identification unit could just transmit a signal to the detection unit in order to activate the displacement sensor, such that the one or more actuators are actuated as soon as a displacement is sensed after the displacement sensor has been activated.

According to an embodiment, the displacement sensor includes an optical position sensor, a mechanical sensor or an acceleration sensor which is arranged in or on the sealing portion.

One example for an optical position sensor is a CMOS sensor. It shall be noted that the displacement sensor does not necessarily need to be arranged directly in or on the sealing portion, but may also be arranged in or on other parts of the patient interface. A mechanical sensor could be, for example, realized as a fine 'hair'-like structure that is attached to the mask on one end and touches the user's face on the other end. When the relative position of the mask and face move this would move the hair-like sensor.

According to a further embodiment, the detection unit further comprises a first pressure sensor for generating a pressure signal including information on a pressure at the interface between the patient interface and the patient's face, wherein the control unit is configured to actuate the one or more actuators based on the displacement signal and the first pressure signal.

By measuring the pressure between the patient interface and the patient's face the exact pressure for optimum performance can be achieved or readjusted by means of the actuators in case the position of the patient interface is unintentionally shifted during sleep. This may especially prevent an unwanted formation of red marks in the patient's face.

According to a further embodiment, the detection unit further comprises a second pressure sensor for generating a second pressure signal including information on a force that is applied to the patient interface from outside by an external object, wherein the control unit is configured to actuate the one or more actuators based on the displacement signal and the second pressure signal.

This second pressure sensor may, for example, include an array of pressure sensors that are disposed on an exterior surface of the patient interface. If the patient turns his head during sleep and presses the patient interface against an external obstacle, this may be sensed by means of the second pressure sensor. The actuators may then adjust the position of the sealing portion of the patient interface in response to these sensed signals. This may further improve the position adjustment.

In a further embodiment, the sealing portion comprises a cushion element and a mask shell for holding the cushion element, wherein the one or more actuators are arranged between the cushion element and the mask shell in order to adjust the position of the cushion element relative to the mask shell and with respect to the patient's face during use. In this embodiment only the cushion element will be readjusted if a displacement is detected, while the mask shell may remain in its displaced position.

In an alternative embodiment, the sealing portion comprises a cushion element and a mask shell for holding the cushion element, wherein the patient interface further comprises an intermediate structure that comprises one or more attachment elements for attaching a headgear to the intermediate structure, wherein the one or more actuators are arranged between the intermediate structure and the mask shell in order to adjust the position of the mask shell and the cushion element relative to the intermediate structure and with respect to the patient's face during use.

In contrast to the above-mentioned embodiment not only the position of the cushion element will be readjusted, but the position of the whole mask (the parts of the mask including the cushion element and the mask shell). The mentioned intermediate structure that couples the mask shell to the headgear straps may be realized as a rigid frame or chassis. Since the actuators are arranged between this rigid frame/chassis and the mask, the headgear straps just hold the chassis in place, such that the strap tightness is de-coupled from achieving a good seal, so that it is easier to achieve comfort. This specifically provides the advantage that the position of the mask shell and the cushion element may be adjusted in an easier way, while the position of the chassis and the headgear may remain the same.

In both of the above-mentioned two embodiments (with and without chassis) the one or more actuators are preferably configured to position at least parts of the sealing portion along three spatial directions including a direction perpendicular to the interface between the patient interface and the patient's face. The sealing portion may therefore be moved/adjusted along all spatial dimensions by means of the one or more actuators, i.e. not only in lateral direction with respect to the interface between the patient interface and the patient's face (x- and y-direction), but also perpendicular thereto (in z-direction). This also allows lifting the sealing portion from the patient's face when correcting its position. Especially in case a chassis is provided, as mentioned above, the patient interface, in particular the sealing portion, may be easier repositioned in xy-direction after having been lifted in z-direction. On the other hand, the mask shell and the cushion element may be automatically lifted/removed from the patient's face after a certain amount of therapy duration, such that a red mark formation in the patient's face is prevented due to a too long wearing of the patient interface.

In a further embodiment, the detection unit may further comprise a sleep detector for sensing a sleep condition signal including information on a sleeping condition of the patient, wherein the control unit is configured to actuate the one or more actuators based on the displacement signal and the sleeping condition signal.

This allows, for example, to lift the cushion element and the mask shell off the patient's face during wakefulness or REM sleep where an OSA treatment is not necessarily needed. However, it shall be noted that the cushion element and the mask shell may also be lifted off the patient's face during other sleep phases when the OSA treatment is not needed. The sleeping condition may, for example, be sensed by means of a photo-plethysmographic sensor (PPG sensor) which senses the pulse of the patient during sleep. This PPG sensor could be integrated into the cushion element.

In an embodiment, the patient interface further comprises a headgear including a plurality of headgear straps for donning the sealing portion to the patient's face, wherein the one or more actuators are configured to position at least parts of the sealing portion relative to the patient's face by individually adjusting one or more of the plurality of headgear straps.

The one or more actuators may, for example, be realized as electric motors that electrically adjust the tension or the position of the one or more headgear straps. Alternatively, the headgear straps may include an electro-active polymer that upon activation changes the tension of individual parts of the headgear.

In an embodiment, the displacement sensor may also be arranged in or on the headgear. The displacement sensor in this case senses a displacement of the sealing portion of the patient interface in directly by sensing a displacement of the headgear.

In all of the above-mentioned embodiments, it is preferred that the control unit is configured to calculate a magnitude and direction of a force necessary to be applied by the one or more actuators for adjusting the position of at least parts of the sealing portion with respect to the patient's face during use in order to return the sealing portion into the identified reference position.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1A:
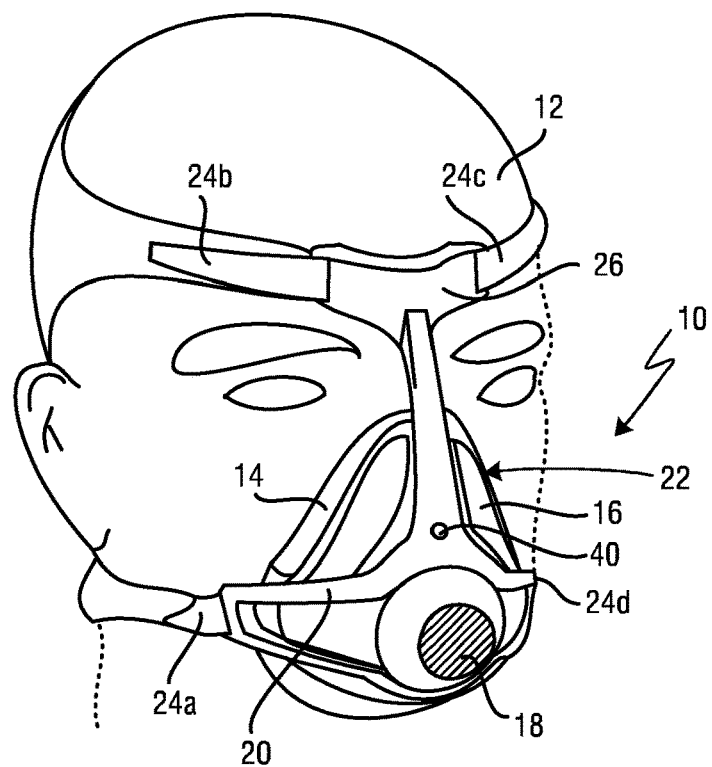
FIG. 1 shows a first embodiment of a patient interface according to the present invention in a schematic perspective view donned to the patient's face (FIG. 1A) as well as in a view from rear (FIG. 1B)

FIGS. 1-6 show four embodiments of a patient interface according to the present invention. The patient interface is therein in its entirety denoted by reference numeral 10.

Figure 1B:
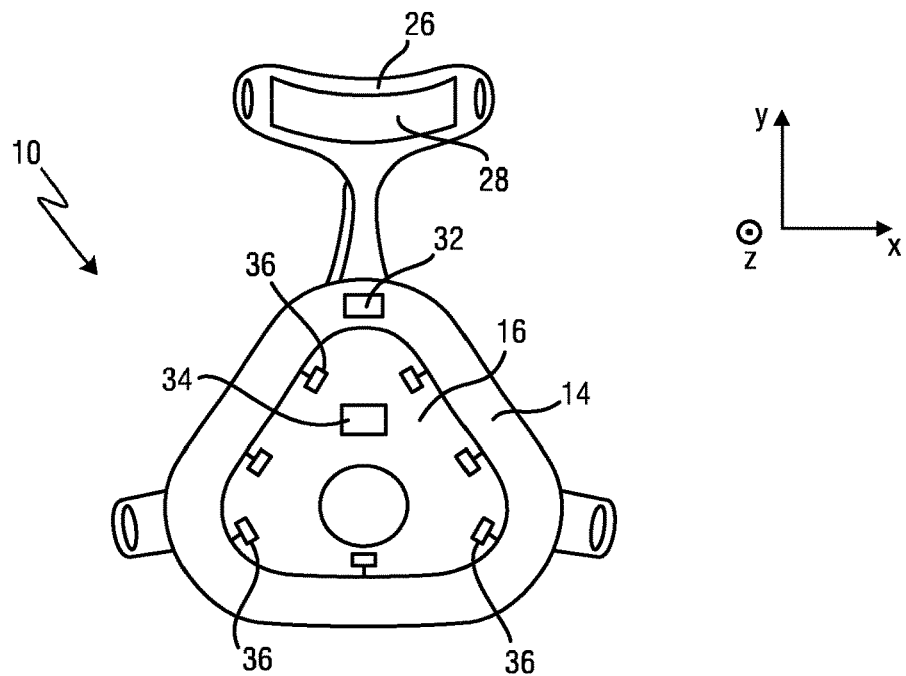

FIGS. 1A and 1B show a first embodiment of the patient interface 10. In this embodiment the patient interface 10 is designed as a full-face mask covering the mouth and the nose of a patient 12. It shall be noted that the patient interface 10 may also be designed as a nose mask, a mouth mask or as a total face mask without leaving the scope of the present invention. According to the first embodiment shown in FIGS. 1A and 1B, the patient interface 10 comprises a cushion element 14 and a mask shell 16. The cushion element 14 is designed to contact the face of the patient 12 and to provide an airtight seal at the interface between the patient's face and the patient interface 10. The cushion element 14 is usually comprised of a soft material, like silicone or any other rubber or suitable elastic material. The mask shell 16 provides a flexible, semi-rigid or rigid support structure for holding the cushion element 14. The mask shell 16 is usually connected to the backside of the cushion element 14, wherein the backside is meant to denote the side of the cushion element 14 opposite to the side of the cushion element 14 contacting the patient's face during use. The mask shell 16 may either be releasably or fixedly connected to the cushion element 14. The cushion element 14 and the mask shell 16 thus together form a cavity which is in this case designed to receive the mouth and the nose of the patient 12. This is herein denoted as sealing portion 22 of the patient interface 10. It shall be noted that the sealing portion 22 does not necessarily have to be formed from two separate parts (the cushion element 14 and the mask shell 16), since the cushion element 14 and the mask shell 16 may be formed as one integral piece.

On the opposite side directing away from the patient's face, the mask shell 16 preferably comprises a connector 18. Via this connector the patient interface 10 may be connected to a hose (not shown) via which a pressurized flow of breathable gas can be submitted to the patient interface 10. The mask shell 16 is further connected to a headgear 20. This headgear 20 preferably includes a plurality of headgear straps 24a-d for donning the mask shell 16 and the cushion element 14 to the patient's face. The headgear 20 may further comprise a forehead support 26 including a forehead cushion 28. This forehead support 26 allows to stabilize the patient interface 10 while being donned to the patient's face and thereby reduces the pressure that is exerted onto the patient's nose during use.

As shown in FIG. 1B, the patient interface 10 according to the first embodiment further comprises a displacement sensor 32 as part of a detection unit 30, a control unit 34 and a plurality of actuators 36. Still further, the patient interface 10 according to the first embodiment may comprise a storage unit 38 and an input interface 40.

Figure 2:
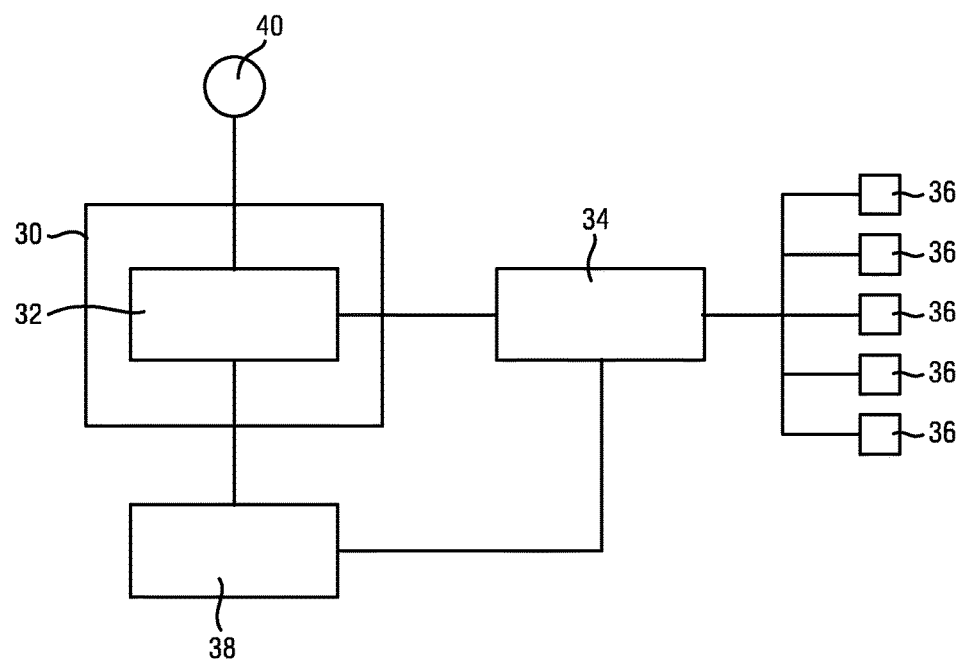
FIG. 2 shows a schematic block diagram illustrating a way of controlling a plurality of actuators arranged in the patient interface according to the first embodiment.

FIG. 2 schematically illustrates in a block diagram how the aforementioned components are preferably connected to each other. The displacement sensor 32 generates a signal including information on a displacement of the sealing portion 22 with respect to the patient's face relative to an identified reference position of the sealing portion 22 with respect to the patient's face. This displacement sensor 32 may, for example, comprise an optical position sensor or an acceleration sensor that measures a displacement relative to an optimal position of the sealing portion 22 with respect to the patient's face. This optimal position of the sealing portion 22, which is taken as a reference position for the displacement sensor 32, may according to the first embodiment shown in FIGS. 1 and 2 be identified in a manual way. As soon as the patient interface 10 is donned to the patient's face in a correct manner such that an airtight seal is formed at the interface between the cushion element 14 and the patient's face without any occurring gas leakages, the patient 12 or any other person (e.g. a physician) may actuate the input interface 40. Upon activation of the input interface 40 the detection unit 30 will receive the information that the patient interface 10 is correctly arranged with respect to the patient's face. In response thereto, the detection unit 30 identifies the current position of the sealing portion 22 with respect to the patient's face, such that the position parameters recorded by the displacement sensor 32 will then be saved in the storage unit 38 as reference parameters belonging to the optimal reference position. The input interface 40 so to say initiates the measurement.

The input interface 40 may be realized as a small button that is either arranged on the patient interface 10 or separately provided and connected to the detection unit 30 and/or the control unit 34 by means of a wireless or wired connection. After the measurement has been initiated in the above-mentioned way, the displacement sensor 32 will generate a displacement signal which includes a current positional information of the sealing portion 22 relative to the identified reference position. If the displacement sensor 32 detects a position change, the control unit 34 will actuate the one or more actuators 36 based on the displacement signal provided by the displacement sensor 32 in order to adjust the position of at least parts of the sealing portion 22 with respect to the patient's face. In other words, the control unit 34 will then calculate a magnitude and direction of a force necessary to be applied by the one or more actuators 36 for readjusting at least parts of the sealing portion 22, such that the patient interface 10 is repositioned again in its optimal position where no gas leakages occur. The control unit 34 may be realized as a microchip that may be directly integrated into the patient interface 10. Alternatively, the control unit 34 may be realized as an external processing unit that is locally separated from the patient interface 10 and connected to the detection unit 30, the storage unit 38 and/or the input interface 40 by means of a wireless or hard-wired connection.

The above-mentioned mechanism allows readjusting the position of the patient interface 10, or at least the position of parts of the sealing portion 22, while the patient interface 10 is donned to the patient's face. If the position of the patient interface 10 is unintentionally shifted during use, e.g. because the patient 12 turns his head during sleep and shifts the position of the patient interface 10 unintentionally with his/her pillow, the actuators 36 will automatically bring the patient interface 10 back into its optimal/reference position, the positional parameters of which have been saved in the storage unit 38.

The actuators 36 are preferably configured to position at least parts of the sealing portion 22 along all three spatial directions x, y and z, i.e. not only in x- and y-direction parallel to the mask-to-patient interface, but also perpendicular to the interface between the patient interface 10 and the patient's face (in z-direction). The actuators 36 may be realized as small electromechanical motors. Alternatively, the actuators 36 may comprise one or more electro-active polymers that may be activated by means of small electrical pulses. The actuators 36 may, for example, be arranged between the cushion element 14 and the mask shell 16 (as shown in FIG. 1B). In this case, the actuators 36 could form the connection between the cushion element 14 and the mask shell 16. However, it shall be noted that the position of the actuators 36 shown in FIG. 1B is only one of multiple possible positions. The actuators 36 could also be arranged between the headgear 20 and the mask shell 16, such that not only the cushion element 14 may be repositioned with respect to the mask shell 16, but the whole sealing portion 22 (including the cushion element 14 and the mask shell 16) may be repositioned with respect to the headgear 20.

Figure 3A:
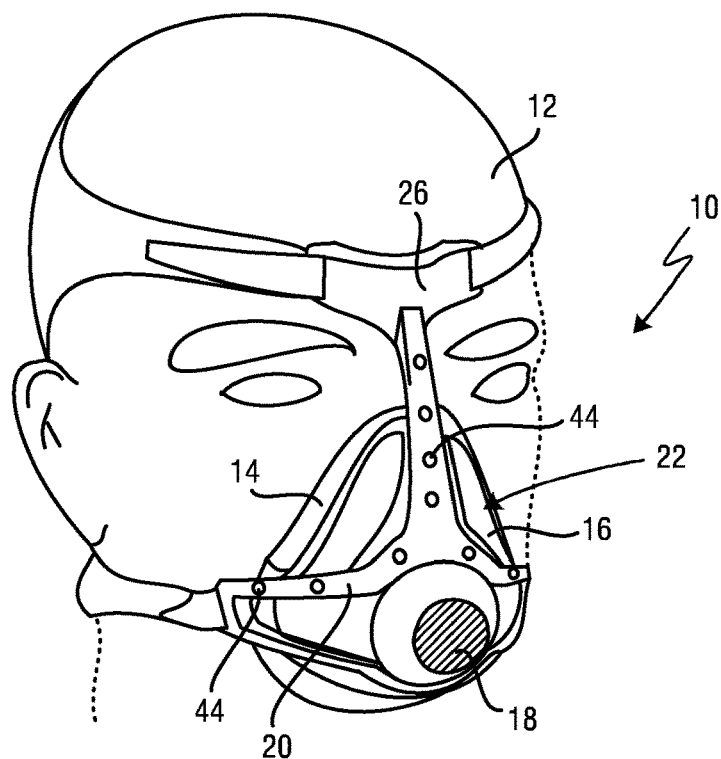
FIG. 3 shows a second embodiment of the patient interface according to the present invention in a schematic perspective view donned to the patient's face (FIG. 3A) as well as in a view from the rear (FIG. 3B)
Figure 3B:
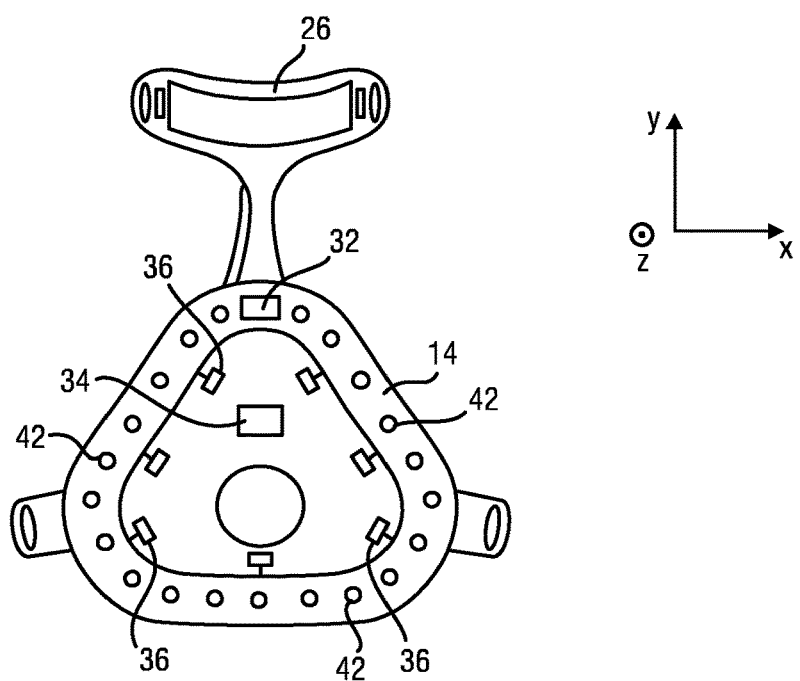
Figure 4:
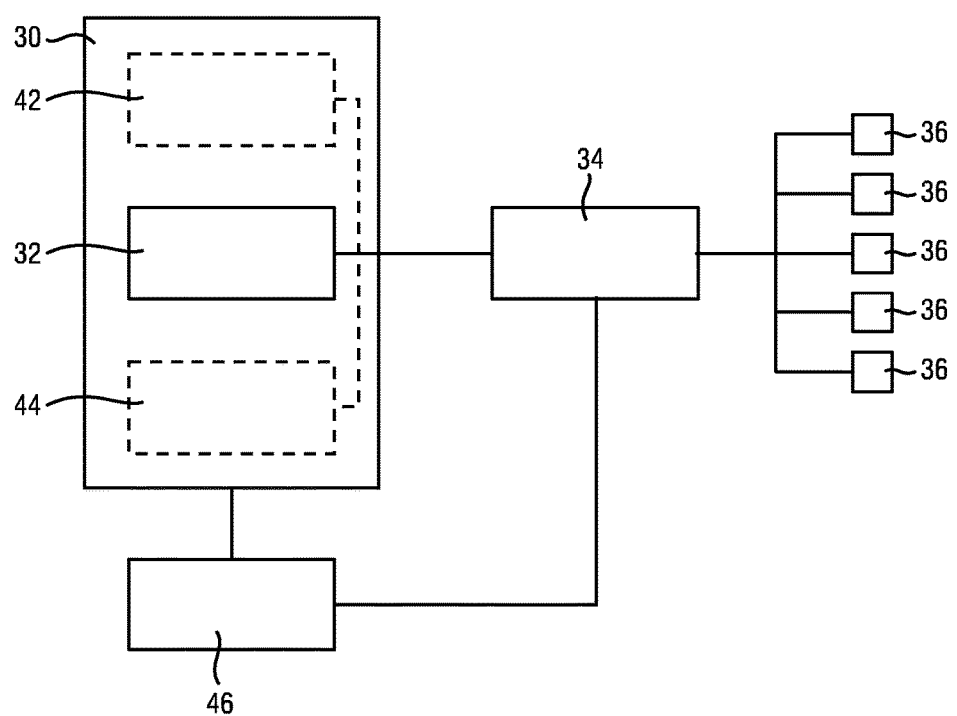
FIG. 4 shows a schematic block diagram illustrating a way of controlling the plurality of actuators arranged in the patient interface according to the second embodiment.

FIGS. 3A and 3B show a second embodiment of the presented patient interface 10. FIG. 4 shows a schematic block diagram 4 illustrating the type of signal processing according to this second embodiment. In addition to the first embodiment shown in FIGS. 1A and 1B the patient interface 10 may further comprise a set of first pressure sensors 42 (see FIG. 3B) and a set of second pressure sensors 44 (see FIG. 3A). The first pressure sensors 42 may generate a first pressure signal including information on a pressure and/or pressure distribution at the interface between the cushion element 14 and the patient's face. The second pressure sensors 44 may generate a second pressure signal including information on a force that is applied to the patient interface 10 from outside by an external object, e.g. by a pillow or other obstacle. The first pressure sensors 42 may be arranged on or within the cushion element 14. The second pressure sensors 44 are preferably arranged on an exterior surface of the patient interface 10, e.g. on an exterior surface of the headgear 20 (as shown in FIG. 3A) or on an exterior surface of the sealing portion 22.

The control unit 34 actuates the one or more actuators 36 according to the second embodiment not only based on the displacement signal provided by the displacement sensor 32, but also based on the first and/or the second pressure signal. This further refines the readjustment of the position of the sealing portion 22, since the first pressure sensors 42 will deliver information about a change in the pressure distribution at the interface between the patient interface 10 and the patient's face, and since the second pressure sensors 44 will provide information from where and to what extent external forces act from outside onto the patient interface 10.

It shall be furthermore noted that no input interface is provided according to this second embodiment. A storage unit 38 does also not necessarily have to be provided. Instead, the patient interface 10 may comprise an identification unit 46 (see FIG. 4) which automatically identifies the reference position of the sealing portion 22 with respect to the patient's face when the patient interface 10 is worn by the patient 12. This identification unit 46 may be connected to the displacement sensor 32 of the detection unit 30. The identification unit 46 is preferably also connected to the control unit 34. An automatic identification of the reference position (the optimal position) of the sealing portion 22 may be implemented as follows: The displacement sensor 32 could comprise an optical sensor, such as e.g. a CMOS sensor, which allows to automatically identify certain landmarks or facial characteristics within the patient's face. The optical sensor 32, for example, visually detect the nose bridge of the patient 12. As soon as certain parts of the sealing portion 22 are correctly positioned with respect to the nose bridge or other characteristics points in the patient's face, the identification unit 46 may trigger the control unit 34 to start the displacement detection. In other words, the identification unit 46 will then tell the control unit 34 that the patient interface 10 is currently in its optimal position. In case a storage unit 38 is provided (as in the first embodiment), the position parameters of the then identified reference position may be stored as reference parameters, similar as in the way explained with reference to the first embodiment. If the optical sensor 32 then detects a position change, the control unit 34 will calculate the force and direction that is necessary to be applied by the actuators 36 in order to bring the sealing portion 22 back into its optimal position.

The additional information concerning the external forces applied onto the patient interface and the pressure distribution at the mask-to-patient interface which is provided by the first and second pressure sensors 42, 44 may be included into this position readjustment calculation. The first pressure sensors 42 may, for example, measure the force of the cushion element 14 onto the patient's face in z-direction, while the displacement in x- and y-direction is measured by means of the displacement sensor 32. As mentioned above, all measurements always consider the difference containing the results of the calculated values regarding the subtraction of the current values in x-, y- and z-direction from the corresponding values/parameters in x-, y- and z-direction in the optimum position of the sealing portion 22.

Figure 5A:
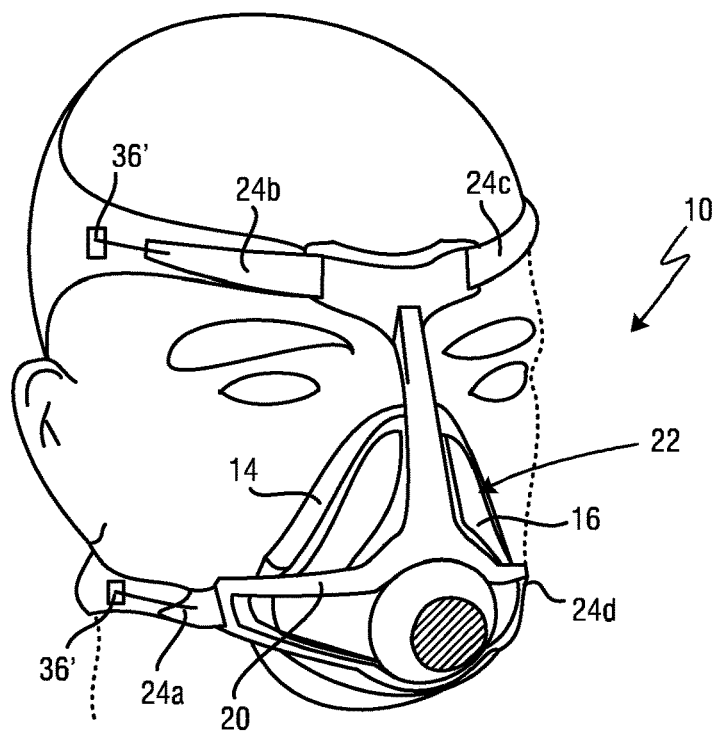
FIG. 5 shows a third embodiment of the patient interface according to the present invention in a schematic perspective view donned to the patient's face (FIG. 5A) as well as in a view from rear (FIG. 5B)
Figure 5B:
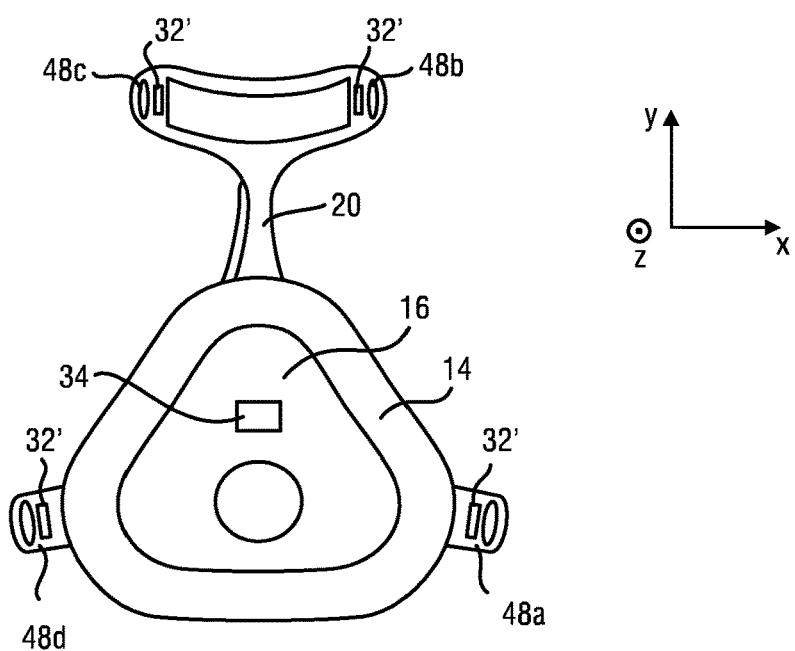

FIG. 5 shows a third embodiment of the patient interface 10 according to the present invention. In this embodiment the displacement of the sealing portion 22 is detected indirectly. The readjustment of the position of the sealing portion 22 is also accomplished in an indirect way. "Indirect" in this case means that the displacement is not directly measured at the sealing portion 22 itself, but at another position. Similarly, the actuators 36' are not directly connected to the sealing portion 22. As shown in FIG. 5B, the detection unit 30 may comprise several displacement sensors 32' which may be arranged at contact points 48a-d at which the mask is connected to the headgear straps 24a-d. The sensors 32' may also comprise force sensors that measure force at the contact points 48a-d. Since these forces or pressures measured by the force sensors 32' also bear information on a displacement of the sealing portion 22, such force or pressure sensors shall also be interpreted as displacement sensor 32' within the meaning of the present invention. The actuators 36' are in this case preferably connected to the individual headgear straps 24a-d. The one or more actuators 36' are thus configured to position the sealing portion 22 or at least parts of it relative to the patient's face by individually adjusting the strength and/or length of the headgear straps 24a-d. This allows modifying the force exerted by each individual headgear straps 24a-d according to the signals sensed by the displacement/force sensors 32'.

The calculation of the position readjustment that is necessary to bring the sealing portion 22 back into its optimal position if it has been unintentionally shifted, may still remain the same as explained above with reference to the first and the second embodiment. The current position of the headgear straps 24a-d or the force at the contact points 48a-d is always measured with respect to the optimal position of the headgear straps 24a-d or the optimal force distribution at the contact points 48a-d. Similar as explained with regard to the first two embodiments, the patient interface 10 may thereto comprise a storage unit 38 for storing the reference parameters. Even though not shown in FIG. 5B the third embodiment may also comprise first and/or second pressure sensors 42, 44 (as explained above with reference to FIGS. 3A and 3B). The values of the force distribution at the mask-to-patient interface, the force distribution within the headgear straps 24a-d and the values of the position of the displacement sensors 32' in the optimal position of the patient interface 10 may again be stored in the storage unit 38. The values of the force measurement in x-, y- and z-directions may then be recorded as current values. The displacement/force sensor 32 will similarly record the position/force values in x- and y-direction as current values. If the embodiment does not have force sensors located with the same x-, y-coordinates as the contact points 48a-d, then for both optimum values and current values the estimated force at each contact point 48a-d is estimated either: (a) linearly by considering the distance between the various force sensors and the contact points 48a-d or (b) non-linearly by taking into account the shape and fit of the sealing portion 22. This data may then be added to the storage unit 38 as additional values. For each measured value the difference between that stored as optimum values and current values may be calculated by subtracting these values. This information may then be stored in the storage unit as measured difference. If the value of the measured difference exceeds a trigger point for either force or displacement, the control unit 34 may perform the following tasks: (a) the magnitude and direction of a counter-force to reduce the difference is calculated in the control unit 34; (b) the control unit 34 may modify the tension in the headgear straps 24a-d individually to create the calculated counter-force necessary to bring the sealing portion 22 back into its optimal position; (c) the values of the measured difference between the current values and the optimum values may then be re-calculated; (d) steps (a)-(c) may be repeated at a "fast time interval" (FTI) until the values in the measured difference is either 0 or below a prescribed level. It shall be noted that the "regular time interval" (RTI), which denotes the time interval the sensor measurements are collected during standard use, may be longer than the "fast time interval" (FTI), which denotes the time interval the sensors measurements are collected during the readjustment of the position of the sealing portion 22.

In case the sensors 32' comprise force sensors, the overall force acting at each contact point 48a-d can be described in terms of orthogonal components of force in x-, y- and z-directions respectively. Depending on the manner the sealing portion 22 is held in place by the headgear straps 24a-d, there may be: (a) the ability or not to modify this force in each direction by changing the strength of each headgear straps 24a-d individually; (b) the ability or not to move the sealing portion 22 in a given direction by means of the actuators 36; (c) the ability or not to lift the sealing portion 22 of the face by releasing the headgear straps 24a-d by means of the actuators 36'.

Furthermore, it shall be noted that the force and/or displacement sensors 32' may be placed at the same location as the contact points 48a-d, so that the force and/or displacement measured by the sensors 32' is the same as that at the contact points 48a-d. Alternatively, the sensors 32' can be placed in locations different to the contact points 48a-d and the force and/or displacement in effect at the contact points 48a-d is derived or estimated in the control unit 34.

Still further, it shall be noted that the headgear straps 24a-d may connect directly to the sealing portion 22. Alternatively, an additional intermediate structure 50 may be provided between the sealing portion 22 and the headgear 20, as this is schematically shown in FIGS. 6A and 6B.

Figure 6A:
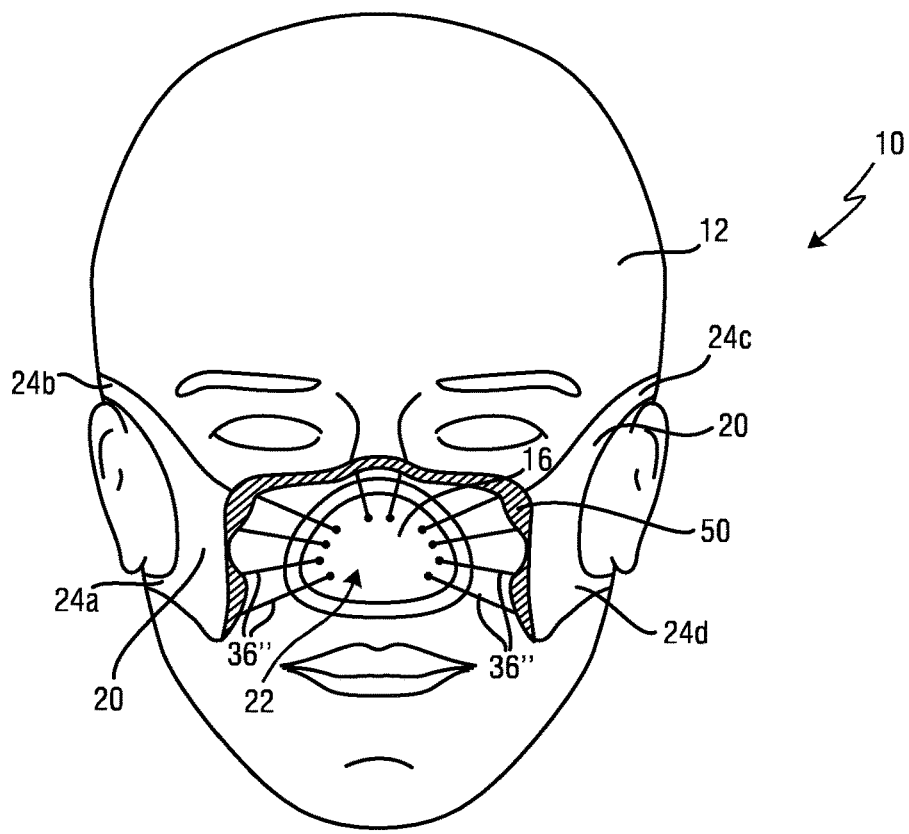
FIG. 6 shows a fourth embodiment of the patient interface according to the present invention in a schematic perspective view donned to the patient's face (FIG. 6A) as well as in a view from rear (FIG. 6B).
Figure 6B:
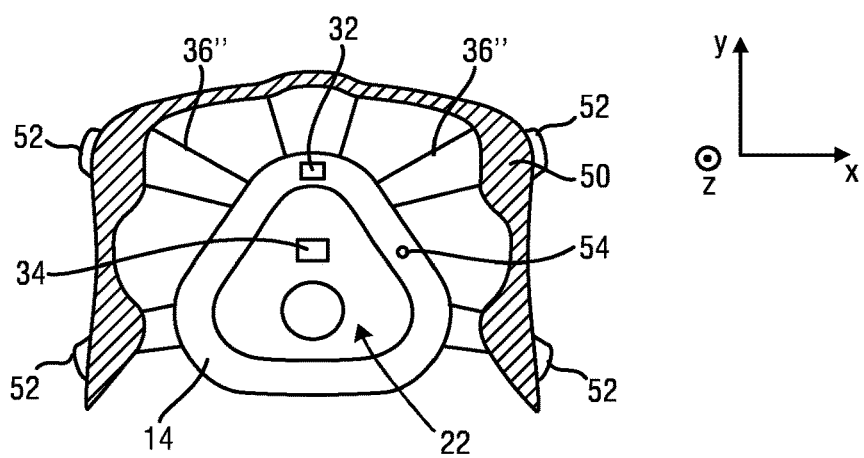

FIGS. 6A and 6B show a fourth embodiment of the patient interface 10 according to the present invention. In this fourth embodiment an intermediate structure 50 is provided which may be realized as a rigid or semi-rigid frame or chassis. The intermediate structure may comprise one or more attachment elements 52 (see FIG. 6B) for attaching the headgear 20 to the intermediate structure. The one or more actuators 36" are in this case preferably arranged between the intermediate structure 50 and the sealing portion 22. The one or more actuators 36" may, for example, connect the intermediate structure 50 with the mask shell 16. This allows readjusting the position of the sealing portion 22 relative to the intermediate structure 50. The actuator 36" may again be realized either as small electromechanical motors or as electro-active polymers.

The main advantage of this fourth embodiment compared to the first three embodiments is that the sealing portion 22 is de-coupled from the headgear 20. In other words, the fixing and position adjustment of the intermediate structure 50 is de-coupled from the fixing and position adjustment of the sealing portion 22. The headgear straps 24a-d in this case only hold the intermediate structure (chassis) in place, such that the strap tightness of the headgear 20 is de-coupled from achieving a good seal at the mask-to-patient interface. Thus, it is easier to achieve comfort.

The sealing portion 22 is preferably connected to the intermediate structure 50 by means of three orientations of electro-active polymer material. This allows to move the mask not only in x-, y-direction, but also to move the sealing portion 22 in z-direction for adjusting the pressure at the mask-to-patient interface. The calculations within the control unit 34 may be realized in the same way as explained above with reference to the first three embodiments.

Due to this decoupling of the sealing portion 22 and the headgear 20, the position and pressure of the sealing portion 22 is de-coupled from the headgear straps 24a-d, which allows a greater choice of strap shape and material. The fourth embodiment furthermore provides an additional advantage: The patient interface 10 may additionally comprise a sleep detection sensor 54 for sensing a sleeping condition signal including information on a sleeping condition of the patient 12. The sleep detection sensor 54 may, for example, be arranged on the cushion element 14 and may comprise a photo-plethysmographic sensor (PPG sensor) for a non-invasive measurement of the pulse of the patient 12 during sleep. The control unit 34 may in this case also be configured to actuate the one or more actuators 36" based on the sleeping condition signal sensed by the sleep detection sensor 54. The actuator 36" may thus move the sealing portion 22 relative to the patient's face in accordance to the sleep stage (e.g. wakefulness, REM sleep). For example, the mask can be lifted from the face of the patient 12 either if a too high pressure at the mask-to-patient interface is measured over a too long time or in case a pressure therapy is not needed in a certain sleep stage. This is especially advantageous if a user has a sensitive skin and a red mark formation shall be prevented. For example, during the REM sleep the apnea hypopnea index (AHI) is anyhow low, such that the sealing portion 22 may be raised in this sleep stage. Thereby, the overall time the sealing portion 22 of the patient interface 10 touches the skin of the patient 12 is reduced, while the effectiveness of the pressure therapy remains the same.

Finally, it shall be noted that the above-mentioned features and components explained with reference to the different embodiments may be combined in a plurality of ways. The fact that some features and components are not visualized in a distinctive embodiment, shall not mean that these features and components may not be combined with this embodiment. The skilled person will realize that a plurality of combinations of the herein shown features and components are possible.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A patient interface for delivering a flow of breathable gas to a patient, comprising:
    a sealing portion for sealing an interface between the patient interface and a patient's face when the patient interface is worn by the patient;
    a detection unit including a displacement sensor for generating a displacement signal including information on a displacement of the sealing portion with respect to the patient's face relative to an identified reference position of the sealing portion with respect to the patient's face;
    one or more actuators for positioning at least parts of the sealing portion relative to the patient's face; and
    a control unit that is configured to actuate the one or more actuators based on the displacement signal in order to adjust a position of at least parts of the sealing portion with respect to the patient's face during use.

2. The patient interface of claim 1, further comprising a storage unit for storing information on the identified reference position of the sealing portion with respect to the patient's face.

3. The patient interface of claim 2, further comprising an input interface which is configured to trigger the detection unit to identify and store in the storage unit the reference position of the sealing portion with respect to the patient's face upon a manual activation of the input interface by the patient.

4. The patient interface of claim 1, further comprising an identification unit for automatically identifying the reference position of the sealing portion with respect to the patient's face when the patient interface is worn by the patient.

5. The patient interface of claim 1, wherein the displacement sensor includes an optical position sensor, a mechanical sensor or an acceleration sensor which is arranged in or on the sealing portion.

6. The patient interface of claim 1, wherein the detection unit further comprises a first pressure sensor for generating a first pressure signal including information on a pressure at the interface between the patient interface and the patient's face, and wherein the control unit is configured to actuate the one or more actuators based on the displacement signal and the first pressure signal.

7. The patient interface of claim 1, wherein the detection unit further comprises a second pressure sensor for generating a second pressure signal including information on a force that is applied to the patient interface from outside by an external object, and wherein the control unit is configured to actuate the one or more actuators based on the displacement signal and the second pressure signal.

8. The patient interface of claim 1, wherein the sealing portion comprises a cushion element and a mask shell for holding the cushion element, wherein the one or more actuators are arranged between the cushion element and the mask shell in order to adjust the position of the cushion element relative to the mask shell and with respect to the patient's face during use.

9. The patient interface of claim 1, wherein the sealing portion comprises a cushion element and a mask shell for holding the cushion element, and wherein the patient interface further comprises an intermediate structure that comprises one or more attachment elements for attaching a headgear to the intermediate structure, wherein the one or more actuators are arranged between the intermediate structure and the mask shell in order to adjust the position of the mask shell and the cushion element relative to the intermediate structure and with respect to the patient's face during use.

10. The patient interface of claim 1, wherein the one or more actuators are configured to position at least parts of the sealing portion along three spatial directions including a direction perpendicular to the interface between the patient interface and the patient's face.

11. The patient interface of claim 1, further comprising a headgear including a plurality of headgear straps for donning the sealing portion to the patient's face, wherein the one or more actuators are configured to position at least parts of the sealing portion relative to the patient's face by individually adjusting one or more of the plurality of headgear straps.

12. The patient interface of claim 1, wherein the control unit is configured to calculate a magnitude and direction of a force necessary to be applied by the one or more actuators for adjusting the position of at least parts of the sealing portion with respect to the patient's face during use in order to return the sealing portion into the identified reference position.

13. The patient interface of claim 1, wherein the displacement sensor is arranged in or on the headgear.

14. The patient interface of claim 1, wherein the detection unit further comprises a sleep detector for sensing a sleeping condition signal including information on a sleeping condition of the patient, and wherein the control unit is configured to actuate the one or more actuators based on the sleeping condition signal and the sleeping condition signal.

15. A pressure support system, comprising:
the patient interface as claimed in claim 1; and
a pressure generator for generating the flow of breathable gas.

* * * * *